(12) United States Patent
Trudel et al.

(10) Patent No.: US 12,121,285 B1
(45) Date of Patent: Oct. 22, 2024

(54) FLEXIBLE BOOT WITH ACTIVE ELECTRODE MONITORING SHIELD FOR FLEXIBLE-WRISTED SURGICAL DEVICES

(71) Applicant: Encision Inc., Boulder, CO (US)

(72) Inventors: Gregory Jude Trudel, Broomfield, CO (US); Michael John Biggs, Denver, CO (US); David Newton, Longmont, CO (US); Philip Schreiber, Boulder, CO (US)

(73) Assignee: Encision Inc., Boulder, CO (US)

( * ) Notice: Subject to any disclaimer, the term of this patent is extended or adjusted under 35 U.S.C. 154(b) by 659 days.

(21) Appl. No.: 17/099,013

(22) Filed: Nov. 16, 2020

Related U.S. Application Data

(63) Continuation of application No. 15/594,197, filed on May 12, 2017, now Pat. No. 10,856,930.

(60) Provisional application No. 62/335,447, filed on May 12, 2016.

(51) Int. Cl.
| | | |
|---|---|---|
| *A61B 18/14* | (2006.01) | |
| *A61B 17/00* | (2006.01) | |
| *A61B 18/00* | (2006.01) | |
| *A61B 18/12* | (2006.01) | |
| *A61B 34/30* | (2016.01) | |
| *A61B 90/00* | (2016.01) | |

(52) U.S. Cl.
CPC .......... *A61B 18/14* (2013.01); *A61B 18/1233* (2013.01); *A61B 34/30* (2016.02); *A61B 90/04* (2016.02); *A61B 2017/00026* (2013.01); *A61B 2018/00083* (2013.01); *A61B 2090/0436* (2016.02)

(58) Field of Classification Search
CPC ..... A61B 18/14; A61B 34/30; A61B 18/1233; A61B 90/04
See application file for complete search history.

(56) References Cited

U.S. PATENT DOCUMENTS

| | | | |
|---|---|---|---|
| 8,551,079 B2 | 10/2013 | Anderson et al. | |
| 2009/0088749 A1* | 4/2009 | Hushka | A61B 18/1445 606/51 |
| 2010/0022950 A1* | 1/2010 | Anderson | A61B 1/00114 604/100.01 |
| 2016/0192980 A1* | 7/2016 | Newton | A61B 90/98 606/34 |

OTHER PUBLICATIONS

Demie, Tigist, "Office Action Regarding U.S. Appl. No. 15/594,197", Jan. 16, 2020, p. 17, Published in: US.

* cited by examiner

*Primary Examiner* — Tigist S Demie
(74) *Attorney, Agent, or Firm* — Neugeboren O'Dowd PC

(57) ABSTRACT

A boot for an electrosurgical instrument has a conductive boot shield substantially enclosed by one or more insulating layers. The boot shield has a flexible conductive medium. The flexible conductive medium has a plurality of conductive components suspended in at least one of a first liquid or a first gel, whereby the boot is configured to bend with a bend radius of about 10 millimeters or less without a loss in conductivity of the boot shield. A related method and system are also provided.

23 Claims, 7 Drawing Sheets

FLEXIBLE BOOT WITH ACTIVE ELECTRODE MONITORING SHIELD FOR FLEXIBLE-WRISTED SURGICAL DEVICES

PRIORITY AND RELATED APPLICATIONS

This application is a continuation application of U.S. application Ser. No. 15/594,197, filed on May 12, 2017, entitled "FLEXIBLE BOOT WITH ACTIVE ELECTRODE MONITORING SHIELD FOR FLEXIBLE-WRISTED SURGICAL DEVICES", and issued as U.S. Pat. No. 10,856,390, which claims the benefit of, U.S. Provisional Application No. 62/335,447, filed on May 12, 2016, entitled "FLEXIBLE BOOT WITH ACTIVE ELECTRODE MONITORING SHIELD FOR FLEXIBLE-WRISTED SURGICAL DEVICES", the entire disclosures of which are incorporated by reference for all proper purposes.

FIELD

The invention relates to electrosurgical procedures, techniques, and devices that utilize enhanced control systems such as robotics and other motion control apparatuses.

BACKGROUND

Electrosurgical systems for minimally invasive surgical procedures utilizing a flexible or articulating wristed device are common in robotic surgical systems or other enhanced control systems. In such systems, a challenge of the design for monopolar instruments is that the elements of the flexing or articulating wrist or other elements of the instrument are at active potential, introducing a risk of unintended patient burns. There remains a need for a device or method that reduces the risk of patient burns, and/or other new and innovative features.

SUMMARY

An exemplary boot for an electrosurgical instrument has a conductive boot shield substantially enclosed by one or more insulating layers. The boot shield has a flexible conductive medium. The flexible conductive medium has a plurality of conductive components suspended in at least one of a first liquid or a first gel, whereby the boot is configured to bend with a bend radius of about 10 millimeters or less without a loss in conductivity of the boot shield.

An exemplary method of retrofitting an electrosurgical instrument includes providing a boot. The boot has a conductive boot shield substantially enclosed by one or more insulating layers. The boot shield has a flexible conductive medium. The flexible conductive medium has a plurality of conductive components suspended therein. The boot is configured to bend with a bend radius of about 10 millimeters or less without a loss in conductivity of the boot shield. The exemplary method further includes placing the boot on an electrosurgical instrument, wherein the placing includes placing the boot over a portion of a shaft of the instrument and a portion of an active element of the instrument. The exemplary method further includes electrically coupling the boot shield to a monitor system. The exemplary method further includes bending the active element relative to the shaft without causing the boot shield to lose conductivity.

An exemplary boot assembly for an electrosurgical instrument includes a boot having a boot shield. A first conductive element is coupled to the boot shield and extends exterior of the one or more insulating layers. The first conductive element may electrically couple the boot shield to a monitor system. The boot shield and a distal portion of the first conductive element are rotatable with a rotating shaft of the electrosurgical instrument relative to a non-rotating portion of the electrosurgical instrument.

DETAILED DESCRIPTION

Figure 1:
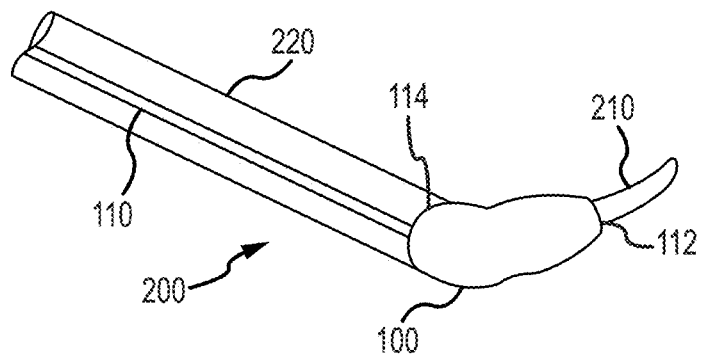
FIG. 1 is a perspective view of an exemplary boot positioned on a surgical tool.

As previously described, there remains a need for a device or method that reduces the risk of patient burns, and/or other new and innovative features. With reference now to FIG. 1, in some embodiments described herein, Applicants provide an insulating boot 100 shaped to be positioned about a linkage in an electrosurgical tool. For example, the tool may have an electrosurgical active element 210 coupled to an instrument shaft 220 by way of an active wrist or other linkage (not shown). The wrist may be configured to enable bending of the active element 210 relative to the shaft 220. The shaft 220 may be configured to rotate the active element 210 relative to a support (not shown) or monitor (not shown). For the purpose of this document, the term "distal" shall be associated with that region of a component approaching or closest to an active element 210, and the term "proximal" shall be associated with that end of a component approaching or closer to a position of a user, support, or robotic control device.

Applicants disclose a boot in co-pending U.S. application Ser. No. 15/070,828, filed on Mar. 15, 2016, and titled "ENHANCED CONTROL SYSTEMS INCLUDING FLEXIBLE SHIELDING AND SUPPORT SYSTEMS FOR ELECTROSURGICAL APPLICATIONS," the entire contents of which are incorporated herein by reference for all proper purposes.

In some embodiments, the boot 100 may include or be coupled to a conductive element 110 to drain energy from the boot 100 to an instrument cable and/or Active Electrode Monitoring monitor (not shown). The conductive element 110 may extend at least a portion of the length of the instrument shaft 220, but those skilled in the art will recognize this is not a requirement.

In some embodiments, the boot 100 is disposable.

The boot 100 may be flexible, to allow movement of the instrument wrist and the active element 210. The boot 100 may comprise an elastomeric material 120, such as silicone or thermoplastic elastomer (TPE). The boot 100 may have a distal end 112 and a proximal end 114, and a longitudinal axis A extending therebetween.

For example, an elastomeric layer may be formed as a boot 100 that may be a stretch fit over the wrist portion of the instrument 200. A low durometer elastomer may be provided to fill in contours of the wrist mechanism. Some embodiments (see e.g. FIG. 2) include a composite construction with a very low durometer elastomer as a first insulating layer 122 and a higher durometer, tougher skin as a second insulating layer 126 to provide resistance to abrasion or cuts. Air spaces can be further reduced by adding a biocompatible medical grade conductive lubricant or gel to the inside of the boot 100.

With air spaces minimized corona heating will be minimized through the use of a low dielectric constant inner insulation such as PTFE in a thickness of between about 0.05 millimeters and 0.15 millimeters. The boot 100 may be configured to operate with a power source (not shown) controlled to have an operating frequency of less than 500 KHz, a peak voltage of less than 3.0 KV, a maximum activation time of 10 seconds, and a duty cycle of less than 30%. With these insulating and driving parameters, a maximum external temperature rise of less than 3 degrees centigrade is achievable.

Figure 2:
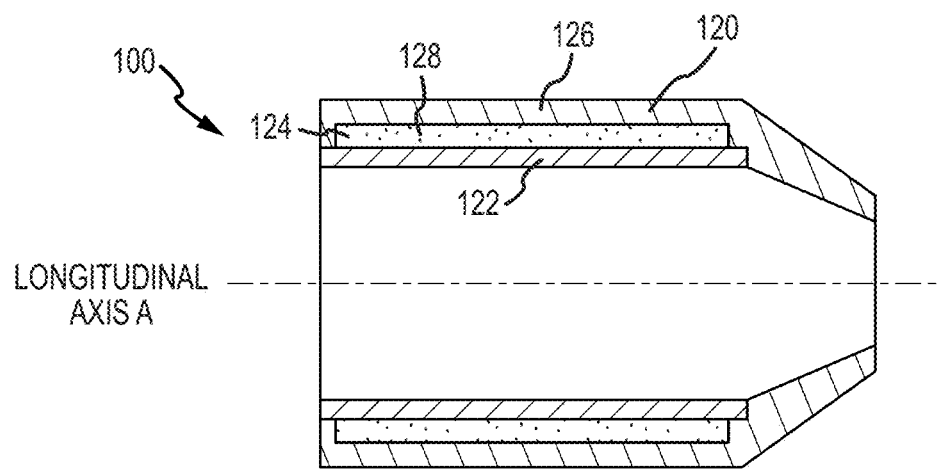
FIG. 2 illustrates a cross section of details of an exemplary boot shield suitable for use in the boot in FIG. 1.

As illustrated in FIG. 2, in some embodiments, the boot 100 may include three or more layers. For example, the boot 100 may have a first insulating layer 122, a second insulating layer 126 positioned exterior of the first insulating layer 122, and a conductive boot shield 124 at least partially positioned therebetween or substantially enclosed by the layers 122, 126. The first insulating layer 122 may be shaped and positioned to separate the boot shield 124 from active current (not shown) traveling through the electrosurgical instrument 200. The first insulating layer 122 should be sufficiently thick to prevent corona heating. In some embodiments, the first insulating layer 122 is at least 0.127 millimeters thick, or more, depending on the properties of the material used and high-frequency potentials applied. The second insulating layer 126 may be shaped and positioned to separate the boot shield 124 from tissue, and to prevent arcing from the active element 210 to the boot shield 124. Specifically, those skilled in the art will recognize that, without a boot 100, energy may tend to pass through tissue adjacent the active element 210 and around the instrument to other elements in the instrument 200. Similarly, energy may tend to pass from the active element 210 through air gaps between the instrument 200 and tissue to other conductive elements in the instrument 200. The boot 100 may insulate conductive elements in the instrument 200 from this unintentional energy transfer.

The first and second layers 122, 126 may be unitary, such as folded or formed about the boot shield 124.

The boot shield 124, positioned between the first and second layers, may be conductive, and may include conductive wires, embedded components, and/or other conductive media. The boot shield 124 may be connected to the conductive element 110, which may include conductive shield wire(s) along the shaft 220.

Some embodiments of the boot shield 124 may include a layer of a flexible conductive medium deposited on a substrate. The substrate may include an elastomeric material, a polymeric material, and/or a flexible fabric 129 (see e.g. FIG. 2A). The medium may be impregnated into or positioned on the substrate, and/or positioned on one or both of the insulating layers 122, 126. The conductive medium may be deposited on the substrate by way of sputter coating, vapor deposition and/or other methods. In some embodiments, the conductive element 110 may be coupled to the conductive medium 128 to form an assembly, and then the assembly may be dip coated to form the second insulating layer 126. In some embodiments, a second elastomeric tube or molding may be slipped over the assembly and bonded at proximal and distal ends of the conductive medium 128 to seal the conductive medium 128 from tissue and active current.

A particular challenge is maintaining conductivity and coverage of the boot shield 124 during flexure of the boot 100. The flexing of the boot 100 may tend to break the material of the conductive medium 128 due to high stress within the conductive medium 128. Moreover, flexing a material with embedded components may modify conductivity of the boot shield 124.

To counter this tendency, the boot shield 124 may be a layer a conductive medium 128 that is not uniform throughout the layer between the first and second insulating layers 122, 126. That is, the conductive medium 128 may be a coating deposited on one or both layers 122, 126 in a pattern, such as a grid, in which the conductive medium 128 is relatively small compared to the thickness of the insulating layers.

In some embodiments, the boot shield 124 may include or be a conductive layer having an elastomeric material embedded with conductive components, such as carbon, silver, and/or other conductive material. The boot shield 124 may be sandwiched between the two insulating layers 122, 126, as described above, or dip coated or over-molded to create insulation all around the boot shield 124.

In some embodiments, the boot shield 124 may include a conductive medium 128 having a thin wire mesh or matrix. In some embodiments, the wire may be braided, or coiled around a distal portion of the boot 100, like a spring. This wire may be bonded to the conductive element 110.

Figure 2A:
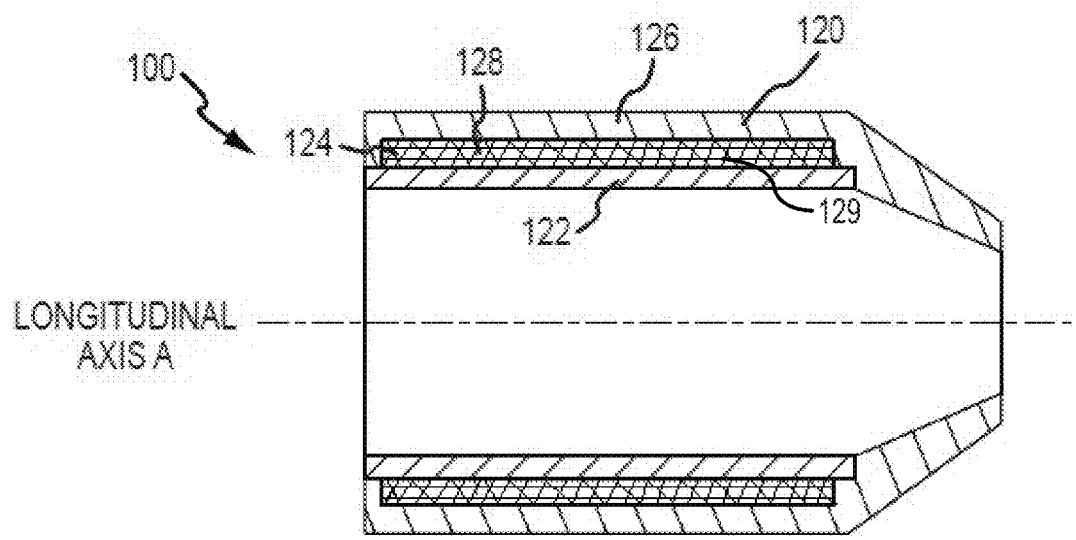
FIG. 2A illustrates a cross section of details of an exemplary boot shield suitable for use in the boot in FIG. 1.

With brief reference to FIG. 2A, in some embodiments, the boot shield 124 may include a conductive medium 128 such as a conductive liquid and/or conductive gel formed on or about or soaked into or deposited onto a substrate; the substrate may be a thin flexible fabric 129. A conductive medium made in this fashion may prevent the liquid and/or gel from being squeezed out of regions between the first and second insulating layers 122, 126.

In some embodiments, the boot shield 124 may include a conductive layer having a liquid or gel medium, such as a conductive liquid or conductive components suspended in a non-conductive medium such as a gel (not shown). In some embodiments, the boot shield 124 may include two liquids that are immiscible, with one of the liquids being conductive. In some embodiments, a liquid and a gel may be provided, with one of the liquid or gel being conductive. In some embodiments, two or more gels may be provided, with at least one gel being substantially non-conductive.

Figure 3A:
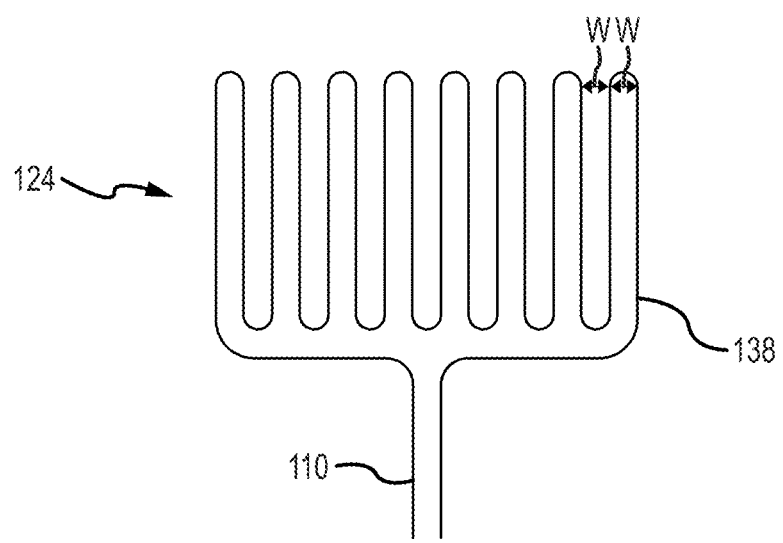
FIG. 3A illustrates an exemplary boot shield suitable for use in the boot in FIG. 1.
Figure 3B:
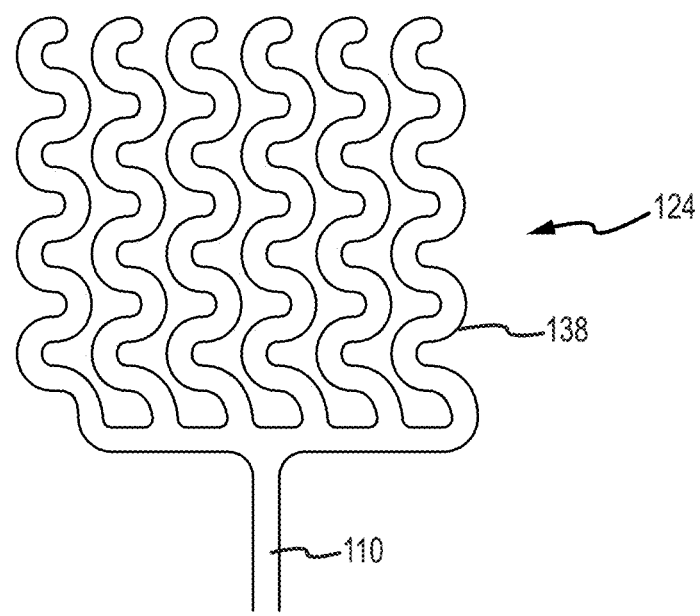
FIG. 3B illustrates an exemplary boot shield suitable for use in the boot in FIG. 1.
Figure 3C:
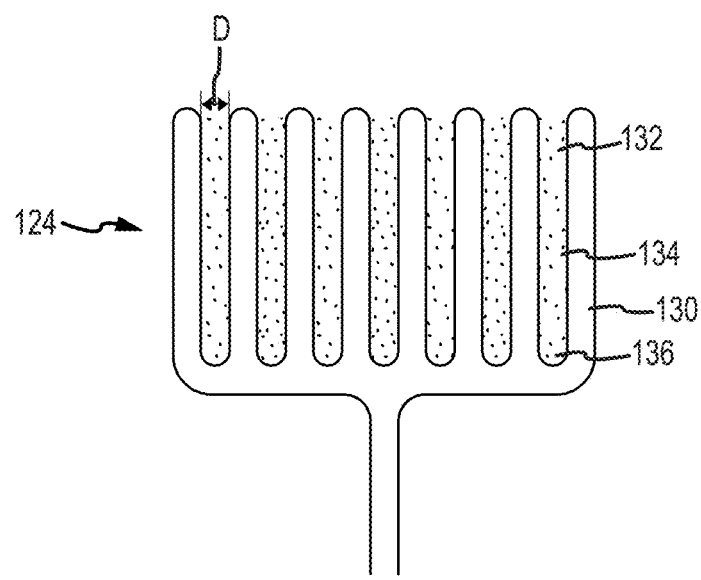
FIG. 3C illustrates an exemplary boot shield suitable for use in the boot in FIG. 1.

In some embodiments, a conductive medium, liquid or gel, is formed by creating a suspension of conductive nanoparticles in a low durometer polymer medium or polymer gel. The conductive nanoparticles may be, for example, silver particles on the order of 20 to 50 nm; however, other conductive materials are contemplated herein. That is, the boot shield 124 may include a flexible conductive medium having a first liquid 134 and/or a first gel 134, and a plurality of conductive components 136 suspended therein (see e.g. FIG. 3C). The plurality of conductive components 136 may be a plurality of conductive particles, a liquid that is immiscible with the first liquid and/or first gel 134, and/or a plurality of gel components that are suspended in the first liquid and/or the first gel 134. Although FIG. 3C illustrates the flexible medium with a liquid or gel 134 and conductive components 136 with an array 130 (to be discussed in more detail below), the array 130 is not present in all embodiments having the liquid/gel 134. Specifically, in some embodiments, the liquid/gel 134 and conductive components 136 may also be impregnated into and/or deposited on a flexible substrate, such as an elastomeric material, a polymeric material, and/or a fabric, such as the substrate or fabric 129 illustrated in FIG. 2A. This may be achieved with a nanoparticle suspension in ink and printed in an array onto the substrate. Further, multiple patterns with varying viscosities or durometers may be applied to achieve the desired conductivity and coverage.

In some embodiments, the boot shield 124 may include a flex circuit 138 or similar wire arrangement, and/or may be formed in a single piece with the conductive element 110. The distal portion of the flex circuit 138 may be an array 138 of conductors that allows sufficient coverage for shielding, but is thin enough to allow flexure of the instrument wrist. The array 138 of conductors may be configured as fingers, feather patterns, or bellows. The array 138 may be deposited such as by way of a spray deposition on one or more of the layers 122, 126.

With reference to FIG. 3C, in some embodiments, the boot shield 124 may have a flexible wire arrangement 130 or array of conductors, with a conductive suspension 132 deposited in gaps between the portions of the wire arrangement 130. The suspension 132 may include a liquid or gel 134 having a plurality of conductive components 136 suspended therein. The combination of a conductive wire arrangement 130 and less conductive suspension 132 may create a preferential conductive pathway, whereby stray energy will couple to the boot shield 124 and not to the patient.

In some embodiments, the conductive element 110 may be a straight flat ribbon, which may be coupled to the shaft 220 using an adhesive strip (not shown) or any suitable coupling mechanism.

If the boot shield 124 has a wire arrangement 130, the maximum spacing D between wire conductors may be about 0.5 millimeters if no conductive suspension 132 is provided. However, if the wire arrangement 130 is in combination with a conductive suspension 132, the spacing D may be greater. In some embodiments, the spacing D is 0.55 millimeters or more. In some embodiments, the spacing D is 1 millimeter or more. In some embodiments, the spacing is 1.5 millimeters or more. In some embodiments, the spacing is 2.0 millimeters or more. In some embodiments, the spacing is 3 millimeters or less. By providing a boot shield 124 with a wire arrangement 130 and a conductive suspension 132, Applicants provide a method in which flexibility of the boot shield 124 is maximized without sacrificing the protective nature (conductivity) of the boot shield 124 or risking fracturing regions of conductivity in the boot shield 124.

The array of thin conductors 130, 138 allows the stresses induced in the conductors 130, 138 by flexing to be sufficiently low that splitting of each conductor is prevented and conductivity is maintained. Turning again to FIGS. 3A-3B, an array example is 0.05 mm conductor width W and separation having 50% coverage. The conductor array 138 may be sandwiched between two insulating layers 122, 126 (see e.g. FIG. 2), and each insulating layer 122, 126 may be about 0.15 mm thick. In some embodiments, the boot 100 is configured to bend on a radius of about 10 millimeters or less while maintaining full conductivity. In some embodiments, the boot 100 is configured to bend on a radius of about 5 millimeters or less while maintaining full conductivity.

Figure 4:
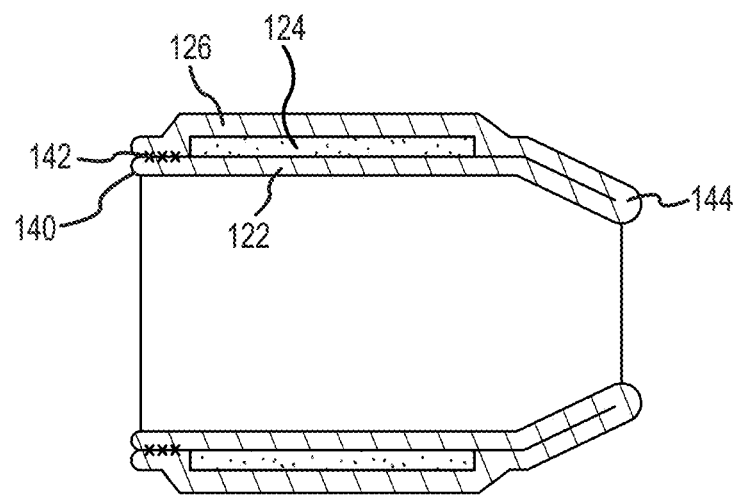
FIG. 4 illustrates a cross section of details of a boot shield suitable for use in the boot in FIG. 1.

With reference now to FIG. 4, one particular challenge is maintaining electrical separation of the boot shield 124 from the active element 210. Any break in insulation (e.g. insulating layer 122) between the boot shield 124 and active current would result in shutdown of the system, as the energy would preferentially transfer to the boot shield 124.

To solve this problem, and as previously alluded herein, one method of production may include positioning the boot shield 124 between two insulating layers 122, 126 and then sealing at least one of the ends 140 of the insulating layers 122, 126 at sealing 142. The end(s) 140 may be sealed using heat, lasers, chemical bonding or adhesive or any other method typically used in the industry.

In some embodiments, and with continued reference to FIG. 4, the first and second insulating layers 122, 126 may be formed of a single tubular material, folded about the boot shield 124 at a first end 144 and sealed at a second end 140 to isolate the boot shield 124 from tissue and the active element 210.

Figure 5:
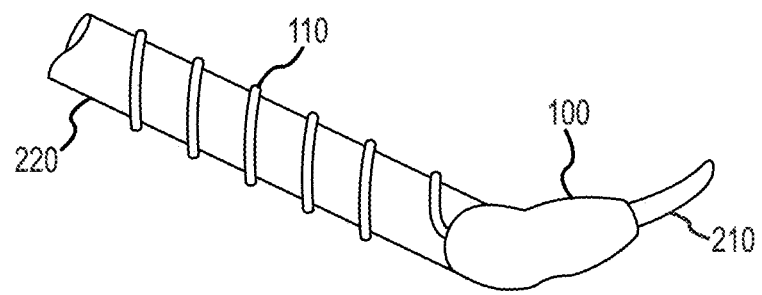
FIG. 5 is a perspective view of an exemplary tool in use with the boot in FIG. 1.

FIG. 5 illustrates the conductive element 110 coupled to the boot shield 124 and wound about the shaft 220, thereby providing excess length for rotation of the shaft 220 relative to a support (not shown).

Figure 6:
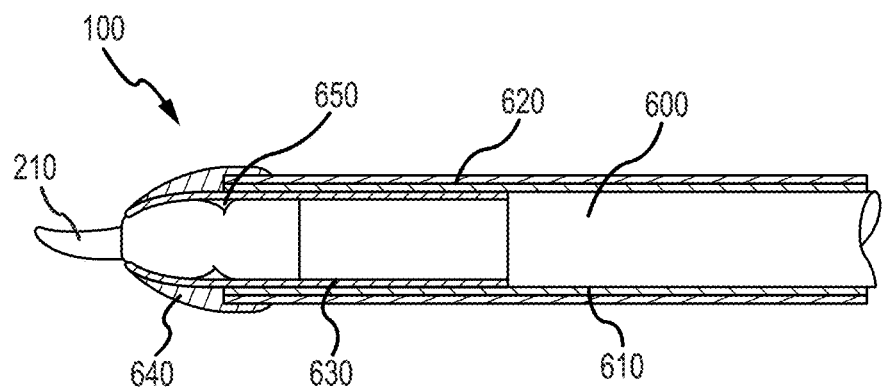
FIG. 6 is a cross section of details of an exemplary boot shield in the boot in FIG. 1.

Turning now to FIG. 6, some embodiments described herein may be configured to minimize or eliminate distance (air) 650 between the boot 630 and the active element 210 of the instrument wrist. For example, the boot 630 may include an outer insulating layer 640 that is unitary with or coupled to an insulating layer 620 that is coupled or adjacent to the shaft 600 of the instrument. A conductive layer 610 may extend between insulating portions 620, 640, of the boot 630.

Some embodiments of the conductive layer 610 may include a thin conductive tube. This layer 610 or tube may provide additional benefit of shielding the instrument shaft as well. The layer 610 or thin conductive tube may not necessarily require an inner insulating layer, as the shaft of the instrument may be insulated as well.

Figure 8A:
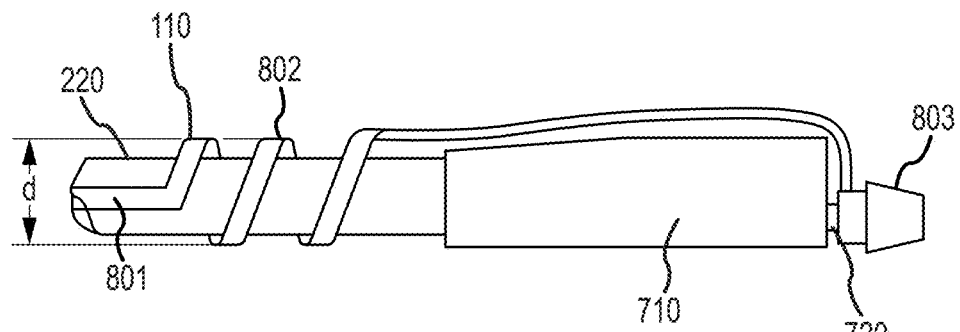
FIG. 8A is a side view of an exemplary connector assembly suitable for use with the tool in FIG. 7 and the boot in FIG. 1.
Figure 8B:
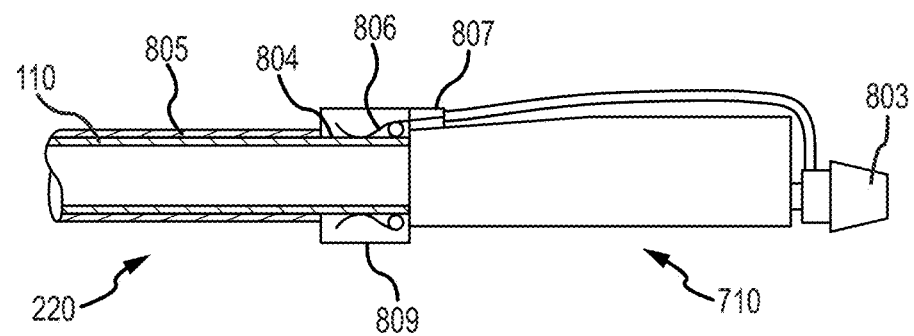
FIG. 8B is a side section view of an exemplary connector assembly suitable for use with the tool in FIG. 7 and the boot in FIG. 1.

With reference now to FIGS. 8A-8B, a particular challenge is that of electrically connecting a sheath or boot 100 on a rotating shaft to a stationary housing. Examples are the Intuitive Surgical Si or Xi instruments, which have a shaft that rotates approximately 540 degrees, but other instruments could rotate 360 to 720 degrees or even have no limitation on rotation. Some embodiments of the invention could include a helical coil at the proximal end, near the instrument housing, that would allow rotation of the shaft, up to 720 degrees. This could be adapted to either a printed flex circuit configuration, where the flex circuit is adhered to the side of the shaft or a simple wire connected to a sheath extending the full length of the shaft.

Figure 7:
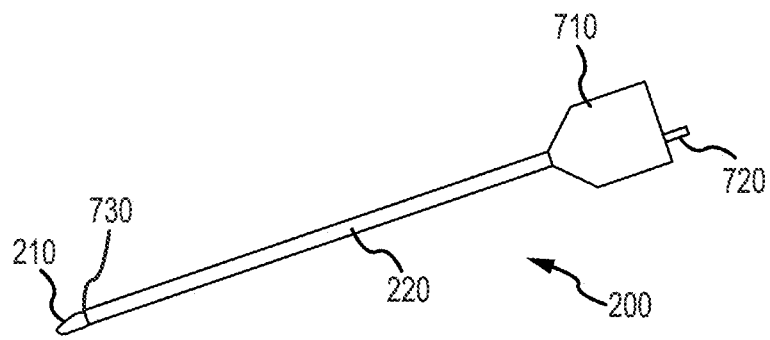
FIG. 7 is a perspective view of an exemplary tool suitable for use with the boot in FIG. 1.

With reference now to FIG. 7, in conjunction with FIGS. 8A-8B, in some embodiments, a boot 100 (see e.g. FIG. 1) may be provided for use with an electrosurgical instrument having a distal end with an active element 210 that is movably or bendably attached to a shaft 220. The shaft 220 may be coupled to or include a housing or shaft connection assembly 710. The shaft connection assembly 710 may include a cable connector 720 for electrically coupling the active element 210 (see e.g. FIG. 1) to a control unit or monitor (not shown). The boot 100, not illustrated in FIG. 7, may be positioned about the linkage 730 between the active element 210 and the shaft 220, and the conductive element 110 may extend towards the connection assembly 710, for coupling to the control or monitor.

As illustrated in FIG. 8A, a proximal structure may include a monitor connector 803 shaped and configured to engage the cable connector 720 associated with the shaft in FIG. 7 to the conductive element 110. The conductive element 110 may include a distal portion 801 and a proximal portion 802. The proximal portion 802 may be wound about the shaft 220 so as to enable the shaft 220 to rotate relative to stationary portions of the device for the housing 710. The distal portion 801 may be attached to the shaft 220. The boot 100 may be electrically coupled to the monitor (not shown) by way of conductive element 110 (see FIG. 1). The connectors 803, 720 may couple the conductive element 110 to the monitor. In some embodiments, the instrument 200 is rotated relative to the housing 710. In some embodiments, the instrument 200 is rotated relative to the monitor, robotics, or other controls and support systems. In some embodiments, the instrument 200 and housing 710 are fixed relative to each other.

In some embodiments, the proximal portion 802 may be wound about the shaft 220 a selected number of times to minimize a change in diameter d of a coiled portion of the conductive element 110 while still allowing enough slack for tightening. The conductive element 110 may be configured to allow up to 720 degrees of rotation of the shaft 220 relative to stationary portions, such as the housing 710.

In some embodiments, a loose sleeve (not shown) or other housing may be provided about the proximal portion 802 to prevent the coils from tangling with or contacting other objects.

With reference now to FIG. 8B, in some embodiments, the shaft 220 may include a brush contact with stationary or non-rotating component features, such as the instrument housing 710. The housing 710 may include one or more brush contacts 806 or a slip ring that electrically connects with the shield or conductive element 110, 804. In this embodiment, instrument arms with unlimited rotation may be provided. The shaft 220 may include an insulating layer 805 surrounding the conductive element 804. A housing 809 may insulate the contacts 806 from other components, and a connector 807 may couple the contacts 806 to the housing 710 and/or the conductive element 110, such as by way of connector 803.

The active element 210 may be shaped and configured to rotate up to 540 degrees about a longitudinal axis relative to the housing 710 and/or other non-rotating portions of the system. In some embodiments, the active element 210 may be shaped and configured to rotate up to 720 degrees about the longitudinal axis relative to the housing 710 and/or other non-rotating portions of the system.

With any embodiment, a connection of the shield must be made to the instrument cable. Any embodiment of the invention may include a connector that adapts to the instrument cable connector. One method to make the connections is a cable connector attached to the shield by a conductor and the cable connector plug in or on the instrument active connector. In some embodiments, the connector is an AEM connector that slips over the banana plug connector of an Intuitive Surgical Si instrument. An AEM cord may then be attached to the connector with the shield and active current input(s). Other instrument types may have different types of connectors, but a similar method may be employed, or various adapters could be manufactured to work with a common shield connector.

Some embodiments of the conducting shield element along the instrument shaft may include the ribbon flex circuit described above. Although it is described above as integrated with a distal flex circuit pattern, the shield element may be combined with any of the above embodiments, for example, connected to another flexible conductive medium.

Some embodiments of the conducting shield element include either a flat ribbon or round wire embedded in a tubular sheath. Utilization of a sheath may eliminate the need to adhere the conductor to the shaft.

Any of the embodiments could be configured as either a sheath that extends the full length of the shaft, a boot that only covers the distal portion of the shaft and instrument wrist, or a combination of the two. The invention could work with an existing non-shielded boot or it could incorporate a boot, replacing the need to install a separate boot.

The use of a conductive element such as the conductive element 110 previously described herein may assist in retaining the boot 100 and may mitigate the risk of the boot 100 falling off into the patient. In some embodiments, a method of retaining a boot by way of a return electrode or conductive element may be provided.

The terms and expressions employed herein are used as terms and expressions of description and not of limitation, and there is no intention, in the use of such terms and expressions, of excluding any equivalents of the features shown and described or portions thereof. In addition, having described certain embodiments, it will be apparent to those of ordinary skill in the art that other embodiments incorporating the concepts disclosed herein may be used without departing from the spirit and scope of the disclosure. Accordingly, the described embodiments are to be considered in all respects as only illustrative and not restrictive.

Figure 9:
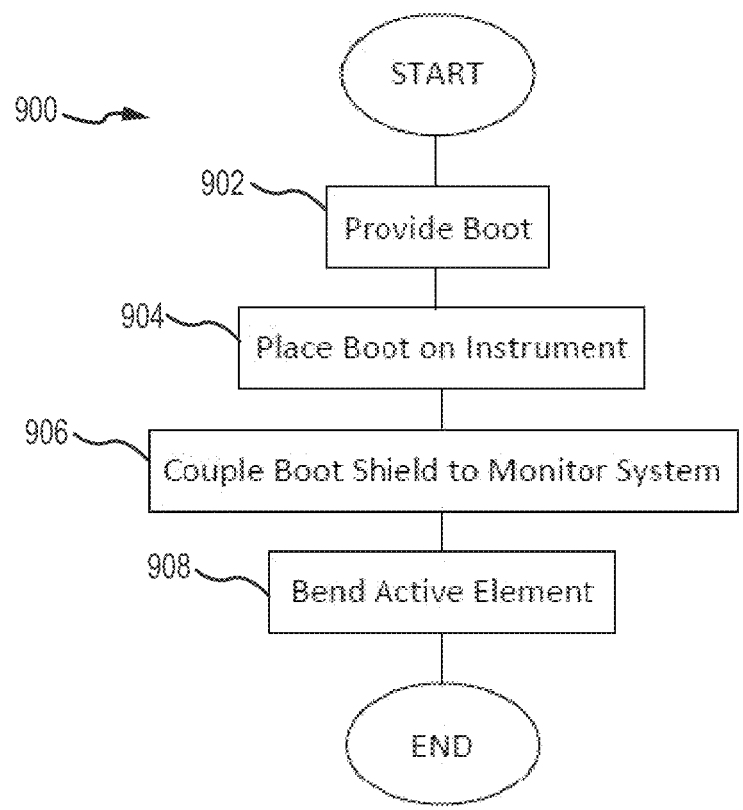
FIG. 9 is a flowchart of an exemplary method.

With reference now to FIG. 9, a method 900 of retrofitting an electrosurgical instrument includes providing 902 a boot. The boot has a conductive boot shield substantially enclosed by one or more insulating layers. The boot shield has a flexible conductive medium. The flexible conductive medium has a plurality of conductive components suspended therein. The boot is configured to bend with a bend radius of about 10 millimeters or less without a loss in conductivity of the boot shield. The method 900 further includes placing 904 the boot on an electrosurgical instrument, wherein the placing 904 includes placing the boot over a portion of a shaft of the instrument and a portion of an active element of the instrument. The method 900 may further include electrically coupling 906 the boot shield to a monitor system. The method 900 may further include bending 908 the active element relative to the shaft without causing the boot shield to lose conductivity. The method 900 may be achieved using the boot 100 previously described herein.

Each of the various elements disclosed herein may be achieved in a variety of manners. This disclosure should be understood to encompass each such variation, be it a variation of an embodiment of any apparatus embodiment, a method or process embodiment, or even merely a variation of any element of these. Particularly, it should be understood that the words for each element may be expressed by equivalent apparatus terms or method terms even if only the function or result is the same. Such equivalent, broader, or even more generic terms should be considered to be encompassed in the description of each element or action. Such terms can be substituted where desired to make explicit the implicitly broad coverage to which this disclosure is entitled.

As but one example, it should be understood that all action may be expressed as a means for taking that action or as an element which causes that action. Similarly, each physical element disclosed should be understood to encompass a disclosure of the action which that physical element facilitates. Regarding this last aspect, by way of example only, the disclosure of an active element should be understood to encompass disclosure of the act of activating the element—whether explicitly discussed or not—and, conversely, were there only disclosure of the act of rotating, such a disclosure should be understood to encompass disclosure of a rotating mechanism. Such changes and alternative terms are to be understood to be explicitly included in the description.

The previous description of the disclosed embodiments and examples is provided to enable any person skilled in the art to make or use the present disclosure as defined by the claims. Thus, the present disclosure is not intended to be limited to the examples disclosed herein. Various modifications to these embodiments will be readily apparent to those skilled in the art, and the generic principles defined herein may be applied to other embodiments without departing from the spirit or scope of the invention as claimed.

What is claimed is:

1. A boot for an electrosurgical instrument, comprising:
   a first insulating layer;
   a second insulating layer positioned exterior of the first insulating layer;
   a boot shield at least partially positioned between the first and second insulating layers, wherein the first insulating layer is shaped and positioned to separate the boot shield from active current traveling through the electrosurgical instrument, and wherein the second insulating layer is shaped and positioned to separate the boot shield from tissue, the boot shield comprising a highly conductive medium;
   and wherein the boot shield is configured to electrically couple to a conductive pathway;
   and wherein stray energy couples to the boot shield via the conductive pathway comprising a combination of a first element and a second element.

2. The boot of claim 1, wherein the first element comprises:
   a flexible conductor array having a plurality of conductive wires in a wire mesh or matrix arrangement, and wherein the flexible conductive array has a first voltage potential, and wherein the flexible conductor array is configured to electrically couple to the conductive pathway.

3. The boot of claim 2, further comprising:
   a conductive suspension deposited between gaps in the flexible conductor array, wherein the conductive suspension comprises a liquid or gel having a plurality of conductive particles suspended in the liquid or the gel, and wherein the conductive suspension has a second voltage potential.

4. The boot of claim 1, wherein the conductive medium comprises a substrate, and wherein the substrate is selected from a group consisting of an elastomeric material, a polymeric material, and a flexible fabric.

5. The boot of claim 4, wherein the conductive medium is configured to be deposited on the substrate using one or more of sputter coating and vapor deposition.

6. The boot of claim 5, wherein the conductive medium further comprises: a liquid or gel having a plurality of conductive particles suspended in the liquid or the gel.

7. The boot of claim 4, wherein the conductive medium is configured to be deposited on the substrate using of a spray deposition on one or more of the insulating layers.

8. The boot of claim 1, wherein the boot shield is configured to electrically couple to a monitor system via the conductive pathway.

9. The boot of claim 1, wherein the boot is configured to bend with a bend radius under a threshold without a loss in conductivity of the boot shield.

10. The boot of claim 9, wherein one or more of:
    the threshold is 10 millimeters,
    the first insulating layer is anywhere between 0.127 mm and 0.15 mm thick, and
    the second insulating layer is up to 0.15 mm thick.

11. The boot of claim 1, wherein the boot shield includes a flex circuit formed in a single piece.

12. The boot of claim 1, wherein at least one end of the insulating layers is sealed to maintain electrical separation of the boot shield.

13. A boot assembly for an electrosurgical instrument, comprising:
    a first conductive element;
    a boot, the boot comprising:
        a first insulating layer;
        a second insulating layer positioned exterior of the first insulating layer;
        a boot shield at least partially positioned between the first and second insulating layers, wherein the first insulating layer is shaped and positioned to separate the boot shield from active current traveling through the electrosurgical instrument, and wherein the second insulating layer is shaped and positioned to separate the boot shield from tissue, the boot shield comprising:
            one or more first elements of a first voltage potential; and
            one or more second elements of a second voltage potential, wherein the first voltage potential is less than the second voltage potential;
        wherein the first conductive element is configured to electrically couple the boot shield to a monitor system; and
    wherein the second element comprises a substrate, and wherein the substrate is selected from a group consisting of an elastomeric material, a polymeric material, and a flexible fabric, and wherein the first element comprises a conductive medium deposited on the substrate, the conductive medium comprising a liquid or gel having a plurality of conductive particles suspended in the liquid or the gel.

14. The boot assembly of claim 13, wherein the boot shield is electrically coupled at a proximal end to the first conductive element using at least one of the first element and second element.

15. The boot assembly of claim 14, wherein the boot is positioned about a linkage between an active element and a shaft, and wherein the first conductive element extends at least a portion of the length of the shaft, and wherein the second insulating layer is shaped and positioned to prevent arcing from the active element to the boot shield.

16. The boot assembly of claim 15, wherein the first and second insulating layers are formed of a single tubular material, folded about the boot shield at a first end and sealed at a second end to isolate the boot shield from tissue and the active element.

17. The boot assembly of claim 13, wherein the first element comprises:
 a flexible conductor array having a plurality of conductive wires in a wire mesh or matrix arrangement, and wherein the flexible conductive array has the first conductivity, and wherein the flexible conductor array is configured to electrically couple to the first conductive element.

18. The boot assembly of claim 17, further comprising:
 a conductive suspension deposited in gaps between the wire mesh or the matrix arrangement, wherein the conductive suspension comprises a liquid or gel having a plurality of conductive components suspended in the liquid or the gel, and wherein the conductive suspension has the second voltage potential.

19. The boot assembly of claim 13, wherein the boot is configured to be placed over a portion of a shaft of the electrosurgical instrument, including at least a portion of an active element at a distal end of the shaft, and wherein the boot is shaped and sized to minimize or eliminate air gaps between the boot and the electrosurgical instrument.

20. The boot assembly of claim 13 wherein the first conductive element is an active assembly.

21. The boot assembly of claim 13 wherein the first conductive element is a wrist linkage.

22. The boot assembly of claim 13, further comprising an outer insulating layer that is unitary with or coupled to an insulating layer that is coupled or adjacent to a shaft of the electrosurgical instrument.

23. The boot assembly of claim 13, further comprising a helical coil at a proximal end, near an instrument housing, that allows rotation of a shaft of the electrosurgical instrument up to 720 degrees.

* * * * *